(12) United States Patent
DeGiorgio et al.

(10) Patent No.: US 8,700,164 B2
(45) Date of Patent: Apr. 15, 2014

(54) DEVICES, SYSTEMS AND METHODS FOR TREATMENT OF NEUROPSYCHIATRIC DISORDERS

(71) Applicant: The Regents of the University of California, Oakland, CA (US)

(72) Inventors: Christopher DeGiorgio, Valencia, CA (US); Ian A. Cook, Los Angeles, CA (US); Alejandro Covalin, Culver City, CA (US); Patrick R. Miller, Santa Monica, CA (US); Lara Schrader, Pacific Palisades, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/769,074

(22) Filed: Feb. 15, 2013

(65) Prior Publication Data

US 2013/0158626 A1    Jun. 20, 2013

Related U.S. Application Data

(63) Continuation of application No. 12/898,686, filed on Oct. 5, 2010, now Pat. No. 8,380,315.

(60) Provisional application No. 61/248,827, filed on Oct. 5, 2009, provisional application No. 61/289,829, filed on Dec. 23, 2009, provisional application No. 61/305,514, filed on Feb. 17, 2010, provisional application No. 61/354,641, filed on Jun. 14, 2010.

(51) Int. Cl.
  *A61N 1/05* (2006.01)
(52) U.S. Cl.
  USPC .......................................................... 607/45

(58) Field of Classification Search
  USPC ............................................................ 607/45
  See application file for complete search history.

(56) References Cited

U.S. PATENT DOCUMENTS

| | | |
|---|---|---|
| 4,233,986 A | 11/1980 | Tannenbaum |
| 5,540,734 A | 7/1996 | Zabara |
| 6,405,079 B1 | 6/2002 | Ansarinia |
| 6,567,702 B1 * | 5/2003 | Nekhendzy et al. ............ 607/46 |
| 6,954,668 B1 * | 10/2005 | Cuozzo ............................ 607/2 |
| 7,734,340 B2 * | 6/2010 | De Ridder ....................... 607/2 |
| 2002/0077670 A1 | 6/2002 | Archer et al. |
| 2004/0176820 A1 | 9/2004 | Paul |
| 2006/0064140 A1 | 3/2006 | Whitehurst et al. |
| 2006/0173510 A1 | 8/2006 | Besio et al. |
| 2006/0200208 A1 | 9/2006 | Terry, Jr. et al. |
| 2008/0103547 A1 | 5/2008 | Okun et al. |
| 2008/0132980 A1 | 6/2008 | Gerber et al. |
| 2008/0172101 A1 | 7/2008 | Bolea et al. |
| 2009/0048642 A1 | 2/2009 | Goroszeniuk |
| 2011/0106220 A1 | 5/2011 | DeGiorgio et al. |
| 2011/0112603 A1 | 5/2011 | DeGiorgio et al. |
| 2011/0218589 A1 | 9/2011 | DeGiorgio et al. |

* cited by examiner

*Primary Examiner* — George Manuel
(74) *Attorney, Agent, or Firm* — Morgan, Lewis & Bockius LLP; Victor E. Johnson

(57) ABSTRACT

The present disclosure relates to methods, devices and systems used for the treatment of mood, anxiety, post traumatic stress disorder, and cognitive and behavioral disorders (collectively, neuropsychiatric disorders) via stimulation of the superficial elements of the trigeminal nerve ("TNS"). More specifically, cutaneous methods of stimulation of the superficial branches of the trigeminal nerve located extracranially in the face, namely the supraorbital, supratrochlear, infraorbital, auriculotemporal, zygomaticotemporal, zygomaticoorbital, zygomaticofacial, infraorbital, nasal and mentalis nerves (also referred to collectively as the superficial trigeminal nerve) are disclosed herein.

18 Claims, 10 Drawing Sheets

| PULSE DURATION (Usec) | 150us | 200us | 250us |
|---|---|---|---|
| mA'S RECORDED (MAX TOLERATED SETTINGS) | 7.92 | 5.94 | 5.72 |
| ELECTRODE RADIUS(cm) (1.25" DIAMETER ROUND ELECTRODES) | 1.59cm | 1.59cm | 1.59cm |
| SURFACE AREA cm | 7.92cm$^2$ | 7.92cm$^2$ | 7.92cm$^2$ |
| CURRENT DENSITY mA/cm$^2$ | 1 | .75 | .72 |
| MAXIMUM SAFE CURRENT DENSITY AT STIMULATING ELECTRODE mA/cm$^2$ | 25 | 25 | 25 |
| CHARGE DENSITY (A)(pulse)/cm$^2$ =uC/cm$^2$ AT STIMULATING ELECTRODE | .15 | .15 | 0.18 |
| MAXIMUM SAFE CHARGE DENSITY (uC/cm$^2$) AT BRAIN | 10 | 10 | 10 |

FIG.7

DEVICES, SYSTEMS AND METHODS FOR TREATMENT OF NEUROPSYCHIATRIC DISORDERS

CROSS REFERENCE TO RELATED APPLICATIONS

This application is a continuation of U.S. application Ser. No. 12/898,686, filed Oct. 5, 2010, now U.S. Pat. No. 8,380,315 which in turn claims the benefit of: U.S. Application No. 61/248,827, filed Oct. 5, 2009; U.S. Application No. 61/289,829, filed Dec. 23, 2009; U.S. Application No. 61/305,514, filed Feb. 17, 2010; and U.S. Application No. 61/354,641, filed Jun. 14, 2010, and each of the above applications is hereby incorporated by reference as though fully set forth herein.

This application is also related to the following copending applications: U.S. application Ser. No. 12/898,685, filed on Oct. 5, 2010; U.S. application Ser. No. 12/898,675, filed on Oct. 5, 2010; U.S. application Ser. No. 12/895,696, filed on Oct. 5, 2010, and each of the above applications is hereby incorporated by reference as though fully set forth herein.

TECHNICAL FIELD

The present disclosure generally relates to cutaneous neuromodulation devices and systems and methods of using the same. More specifically, methods, devices, and systems configured for the treatment of neuropsychiatric disorders, such as mood, cognitive and behavioral disorders, via trigeminal nerve stimulation ("TNS") are provided. Devices and systems configured for stimulation of superficial sensory branches of cranial nerves and their methods of application are described.

BACKGROUND

Psychiatric or neuropsychiatric disorders, for example depressive disorders (DD) sometimes referred to as depression, or anxiety disorders, are traditionally treated with pharmacotherapy and psychotherapy. However, a substantial percentage of patients with these and other conditions do not recover despite multiple trials of treatment. Traditionally, brain stimulation has been a primary treatment alternative, and electroconvulsive therapy (ECT, or "electroshock" therapy) has been the dominant brain stimulation approach since the first part of the 20th century. ECT carries risks of memory and other cognitive side effects, considerable cost, and risks of anesthesia. Two implantable approaches have also been described: deep brain stimulation (DBS), in which electrodes are implanted directly within the brain, and vagus nerve stimulation (VNS) in which stimulating electrodes are implanted on the vagus nerve in the neck. While the U.S. Food and Drug Administration (FDA) have approved systems for deep brain stimulation for the treatment of Parkinson's disease, DBS is presently an experimental intervention for other neuropsychiatric conditions. The risks of DBS include infection, hemorrhage, and injury to deep brain structures. In reports of clinical studies with VNS, many of the patients who undergo VNS treatments do not achieve remission, and there is no reliable predictor of good outcomes from the implanted VNS device.

SUMMARY

One aspect of the subject matter of the present disclosure addresses the aforementioned needs by providing a method of treating neuropsychiatric disorders and systems and devices configured to stimulate the ophthalmic (supraorbital), infraorbital and mentalis branch(es) of the trigeminal nerve, and more specifically by providing a method of treating neuropsychiatric disorders using trigeminal nerve stimulation (TNS).

In another aspect of the present disclosure, there is provided an electrode assembly configured for the cutaneous stimulation of the trigeminal nerve.

In yet another aspect of the present disclosure, a method of treating neuropsychiatric disorders using the disclosed electrode assembly is provided.

A method of treating a psychiatric disorder in a patient, the method comprising: attaching at least one electrode cutaneously to the patient so as to contact the skin surface overlying the cutaneous distribution of at least one of the branches of the trigeminal nerve; and applying adjustable electric signals to at least one of the patient's trigeminal nerves through the at least one electrode.

An electrode assembly configured to cutaneously stimulate at least one of the ophthalmic or supraorbital afferent of the trigeminal nerves, the device comprises: a first contact configured for placement on the right side of a patient's face; a second contact configured for placement on the left side of a patient's face; and an insulating connection region connecting the first contact and the second contact; wherein the first contact and the second contact are configured to contact a portion of the skin of the patient overlying the cutaneous distribution of at least one branch of the trigeminal nerve.

A method of treating a psychiatric disorder in a patient, comprising: providing an electrode assembly provided in accordance with claim 2; attaching the electrode assembly to the patient so as to contact the skin surface over at least one of the ophthalmic or supraorbital nerve; and applying electric signals to the electrode assembly at a frequency between 20 and 300 Hertz, at a pulse duration between 50 and 250 microseconds, at an output current density of not greater than 25 $mA/cm^2$ and an output charge density of not greater than 10 $\mu Coulomb/cm^2$ at the cerebral cortex.

In another aspect, a system for trigeminal nerve stimulation for treatment of a neuropsychiatric disorder is disclosed herein. In one embodiment, the system includes: a pulse generator and a cutaneous electrode assembly. The cutaneous electrode assembly includes a first electrode comprising at least one contact configured for cutaneous placement at a first region of the patient's face, wherein the first electrode is configured to contact a portion of the patient's face overlying the cutaneous distribution of at least one branch of the trigeminal nerve, wherein the system is configured for minimal current penetration into a brain of a patient, and wherein the at least one branch of the trigeminal nerve is selected from the group consisting of: ophthalmic nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In some embodiments, the system may further include a second electrode comprising at least one contact configured for cutaneous placement at a second region of the patient's face, wherein the second electrode is configured to contact a portion of the patient's face overlying the cutaneous distribution of at least one branch of the trigeminal nerve, wherein the at least one branch of the trigeminal nerve is selected from the group consisting of: ophthalmic nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In some embodiments, the first electrode and the second electrode are configured to contact a portion of the patient's face overlying the cutaneous distribution of a same branch of the trigeminal nerve. In some embodiments, the first electrode and the second electrode are configured to contact a portion of the patient's face overlying the cutaneous distribution of a different branch of the trigeminal nerve. The system may further include a wire operably connecting the pulse generator and the cutaneous electrode assembly. The system may further include a regulating device configured to regulate the maximum charge balanced output current below approximately 30-50 mA. In some aspects, the neuropsychiatric disorder is selected from the group consisting of: mood disorder, cognitive disorder, behavioral disorder and anxiety disorder. In some aspects, the pulse generator is configured to apply electrical signals at a frequency between approximately 20 and 300 Hertz, at a pulse duration between approximately 50 and 500 microseconds, at an output current density of not greater than approximately 25 mA/cm$^2$ and an output charge density of not greater than approximately 10 microCoulomb/cm$^2$.

In another aspect, cutaneous electrode assembly for trigeminal nerve stimulation for treatment of a neuropsychiatric disorder is disclosed. In one embodiment, the assembly includes: a first electrode comprising at least one contact configured for cutaneous placement at a first region of the patient's face, wherein the first electrode is configured to contact a portion of the patient's face overlying the cutaneous distribution of at least one branch of the trigeminal nerve, wherein the assembly is configured for minimal current penetration into a brain of a patient, and wherein the at least one branch of the trigeminal nerve is selected from the group consisting of: ophthalmic nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In some embodiments, the assembly may further include a second electrode comprising at least one contact configured for cutaneous placement at a second region of the patient's face, wherein the second electrode is configured to contact a portion of the patient's face overlying the cutaneous distribution of at least one branch of the trigeminal nerve, wherein the at least one branch of the trigeminal nerve is selected from the group consisting of: ophthalmic nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In one embodiment, the first electrode and the second electrode are configured to contact a portion of the patient's face overlying the cutaneous distribution of a same branch of the trigeminal nerve. In one embodiment, the first electrode and the second electrode are configured to contact a portion of the patient's face overlying the cutaneous distribution of a different branch of the trigeminal nerve. In one embodiment, the neuropsychiatric disorder is selected from the group consisting of: mood disorder, cognitive disorder, behavioral disorder and anxiety disorder.

In another aspect, a method for treating a neuropsychiatric disorder by trigeminal nerve stimulation is disclosed herein. In one embodiment, the method includes contacting a first region of a patient's face with a cutaneous electrode assembly, the cutaneous electrode assembly comprising: a first electrode comprising at least one contact configured for cutaneous placement at a first region of the patient's face, wherein the first electrode is configured to contact a portion of the patient's face overlying the cutaneous distribution of at least one branch of the trigeminal nerve, wherein the assembly is configured for minimal current penetration into a brain of a patient, and wherein the at least one branch of the trigeminal nerve is selected from the group consisting of: ophthalmic nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve; and applying electrical signals to the electrode assembly at specified operational parameters to treat a neuropsychiatric disorder. In some embodiments, the electrode assembly may further include a second electrode comprising at least one contact configured for cutaneous placement at a second region of the patient's face, wherein the second electrode is configured to contact a portion of the patient's face overlying the cutaneous distribution of at least one branch of the trigeminal nerve, wherein the at least one branch of the trigeminal nerve is selected from the group consisting of: ophthalmic nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In one embodiment, the step of applying electrical signals comprises applying electrical signals at a frequency between approximately 20 and 300 Hertz, at a current of 0.05 to 5 milliamperes (mA) and at a pulse duration of less than or equal to 500 microseconds. In one embodiment, the step of applying electrical signals comprises applying electrical signals at a frequency between approximately 20 and 300 Hertz, at a pulse duration between approximately 50 and 500 microseconds, at an output current density of not greater than approximately 25 mA/cm$^2$ and an output charge density of not greater than approximately 10 microCoulomb/cm$^2$ at the cerebral cortex. In one embodiment, the neuropsychiatric disorder is selected from the group consisting of: mood disorder, cognitive disorder, behavioral disorder and anxiety disorder.

In another aspect, a kit for trigeminal nerve stimulation for treatment of a neuropsychiatric disorder is disclosed herein. In one embodiment, the kit includes: the cutaneous electrode assembly as described herein; and instructions for placing the electrode assembly on a patient for treatment of a neuropsychiatric disorder. In some embodiments, the kit may include a pulse generator; and instructions for applying electrical signals to the electrode assembly for treatment of a neuropsychiatric disorder.

BRIEF DESCRIPTION OF THE DRAWINGS

The present disclosure, both as to its organization and manner of operation, together with further objects and advantages, may be understood by reference to the following description, taken in connection with the accompanying drawings, in which:

FIG. 7 summarizes one embodiment of current, charge, current density and charge density parameters for a subject exposed to cutaneous stimulation of the supraorbital nerve.

DETAILED DESCRIPTION

Figure 1:
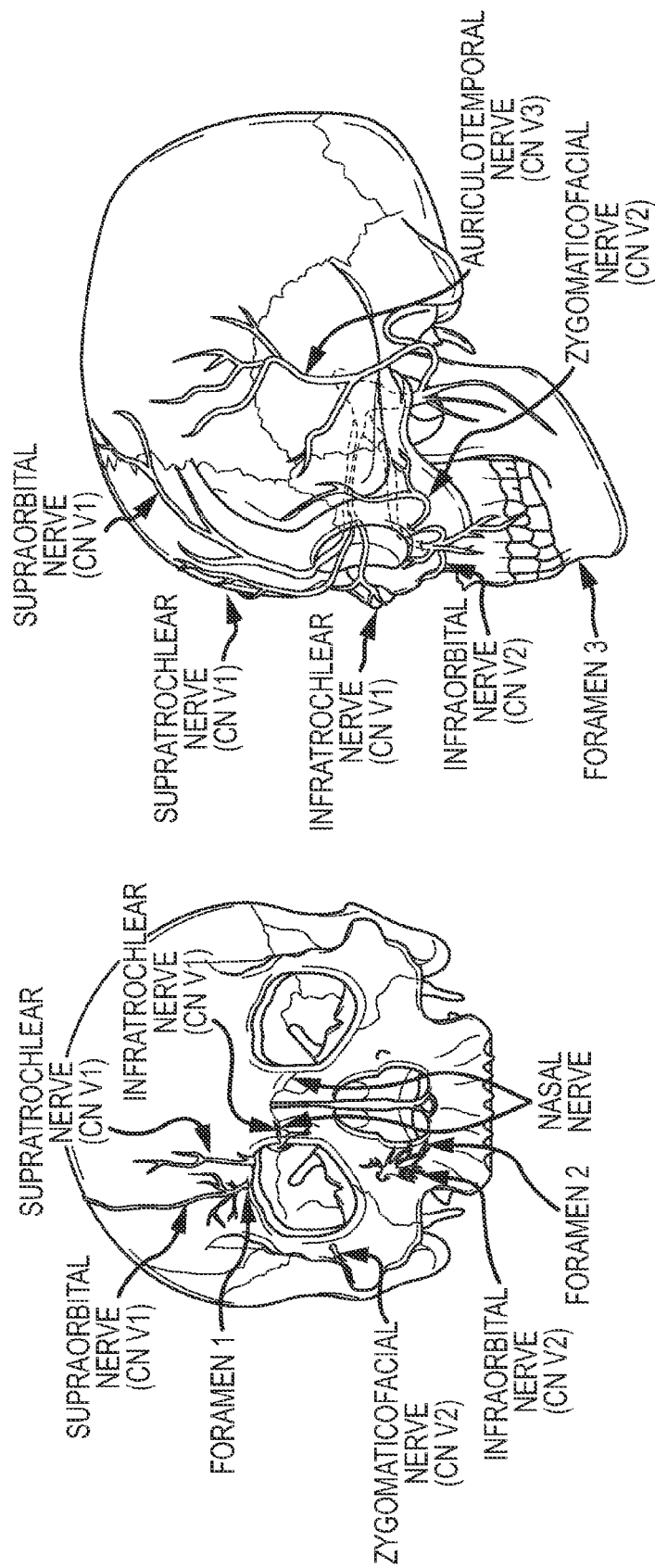
FIGS. 1A and 1B illustrate the location of several branches (nerves) of the trigeminal nerve and the location of the major foramina for the superficial branches of the trigeminal nerve.

The present disclosure relates to methods, devices and systems used for the treatment of mood, anxiety, post traumatic stress disorder, and cognitive and behavioral disorders (collectively, neuropsychiatric disorders) via stimulation of the superficial elements of the trigeminal nerve ("TNS"). More specifically, cutaneous methods of stimulation of the superficial branches of the trigeminal nerve located extracranially in the face, namely the supraorbital, supratrochlear, infraorbital, auriculotemporal, zygomaticotemporal, zygomaticoorbital, zygomaticofacial, infratrochlear, nasal and mentalis nerves (also referred to collectively as the superficial trigeminal nerve) are disclosed herein. Methods for the treatment of mood and other neuropsychiatric disorders by eTNS (external trigeminal nerve stimulation) are also provided. Systems and devices configured for therapeutic stimulation of the trigeminal nerve or branches thereof, such as the superficial trigeminal nerve, and their methods of application are also described. The unique anatomy of the trigeminal nerve, and its direct and indirect connections with key areas of the brainstem, thalamus, amygdala, insula, anterior cingulate and other cortical and subcortical areas involved with sensory processing, attention, emotion, cognition, and autonomic function, may allow the use of external stimulation for a variety of neuropsychiatric conditions in which stimulation may be desirable. The methods, systems and devices described herein may be noninvasive or minimally invasive.

Some brain stimulation methods aim to generate currents in large volumes of the cortex and treat the brain as a bulk conductor, for example, ECT (electroconvulsive therapy) at the whole-lobe level and rTMS (repetitive transcranial magnetic stimulation) at the large regional level (i.e. dorsolateral prefrontal cortex). Additionally, deep brain stimulation is generally predicated on stimulation of small but regional volumes that lead to discharges in a very large number of cells. The systems, devices and methods of the present disclosure send minimal, if any, current into the brain; instead, signals are sent into the brain in order to modify the activity of relevant neuroanatomical structures. Without wishing to be bound by any particular theory, the electrical pulses generate signals in the cutaneous branches of the trigeminal nerve and the electric fields are generally confined to the skin tissue and there is minimal, if any, leakage into the brain. These electrical pulses trigger a cascade of change in neuronal signaling events that involve very limited and precise recruitment of specific networks of neurons. The neuroanatomic pathways allow targeted modulation of activity in areas involved in depression (locus coeruleus, anterior cingulate, insula, amygdala, and other cortical and subcortical structures). Thus, the systems, devices and methods as disclosed herein utilize the brain's existing infrastructure to transmit signals to the targets of interest. In the context of this disclosure, minimal current penetration means (1) a charge density of approximately 0 uC/cm$^2$ at the cerebral cortex, or (2) calculated, measured, or modeled charge densities below the following thresholds at the cerebral cortex: (a) at currents, charge densities, or charge per phase not likely to cause direct activation of pyramidal neurons and axons; and (b) to prevent brain injury, a charge density of less than 10 μC/cm$^2$ in one embodiment, and, in other embodiments, a charge density of less than 1.0 μC/cm$^2$ and in some embodiments, a charge density of less than 0.001 to 0.1 μC/cm$^2$, and at combinations of charge density and charge per phase not known to cause brain injury. In some embodiments, a lower charge density may be used when the central nervous system of an individual patient is sufficiently sensitive to lower levels of stimulation that the lower level will still permit clinical benefit to accrue.

The following description is provided to enable any person skilled in the art to make and use the subject matter of this disclosure. Various modifications, however, will remain readily apparent to those skilled in the art, since the general principles of the disclosed subject matter have been defined herein specifically to describe: (1) methods of treating psychiatric disorders by trigeminal nerve stimulation, (2) a system and an electrode assembly configured for cutaneous trigeminal nerve stimulation; and (3) methods of treating psychiatric disorders using such system and electrode assembly.

With reference to FIGS. 1A and 1B, the trigeminal nerve is the largest cranial nerve, and has extensive connections with brainstem and other brain structures. The trigeminal nerve has three major sensory branches over the face, all of which are bilateral, and highly accessible. The supraorbital nerve, or ophthalmic nerve, is frequently referred to as the V1 division. The infraorbital branch, or maxillary nerve, is commonly referred to as the v2 division. The mandibular nerve (also known as the mentalis branch) is referred to as the v3 division. The supraorbital nerve supplies sensory information about pain, temperature, and light touch to the skin of the forehead, the upper eyelid, the anterior part of the nose, and the eye. The infraorbital branch supplies sensory information about pain, temperature, and light touch sensation to the lower eyelid, cheek, and upper lip. The mentalis branch supplies similar sensory modalities to the skin of the lower face (e.g. jaw and tongue) and lips.

These branches exit the skull through three foramina, as shown in FIGS. 1A and 1B. The supraorbital nerve or ophthalmic nerve exits at foramen 1 (the supraorbital foramen or notch), approximately 2.1-2.6 cm from the nasal midline (in adults), and is located immediately above the orbital ridge that is located below the eyebrow. The infraorbital branch or maxillary nerve exits at foramen 2 (the infraorbital foramen), approximately 2.4-3.0 cm from the nasal midline (in adults), and the mentalis nerve exits at foramen 3 (the mentalis foramen), approximately 2.0-2.3 cm from the nasal midline (in adults). The nasal nerve is a division of the ophthalmic nerve. Other sensory branches, including the zygomaticofacial, zygomaticoorbital, zygomaticotemporal, and auriculotemporal, arise from other foramina.

Fibers from the three major branches join together to form the trigeminal ganglion. From there, fibers ascend into the brainstem at the level of the pons to synapse with the main sensory nucleus of the pons, the mesencephalic nucleus of V, and the spinal nucleus and tract of V. Pain fibers descend in the spinal nucleus and tract of V, and then ascend to the ventral posterior medial nucleus (VPM) of the thalamus. Light touch sensory fibers are large myelinated fibers, which ascend to the ventral posterior lateral (VPL) nucleus of the thalamus. Afferent sensory fibers project from the trigeminal nuclei to the thalamus and the cerebral cortex.

The trigeminal nucleus has reciprocal projections to the nucleus tractus solitarius (NTS), the locus coeruleus, the cerebral cortex and the vagus nerve. The NTS receives afferents from the vagus nerve and trigeminal nerve. NTS integrates input from multiple sources, and projects to structures in the brainstem and forebrain, including the locus coeruleus.

The locus coeruleus is a paired nuclear structure in the dorsal pons, and is located just beneath the floor of the fourth ventricle. The locus coeruleus has extensive axonal projections to a broad number of brainstem, sub-cortical and cortical structures, and is an important part of the reticular activating system. The locus coeruleus is a core part of the brainstem noradrenergic pathway, and produces the neurotransmitter norepinephrine. Norepinephrine plays a key role in attention, alertness, blood pressure and heart rate regulation, and mood.

While not wishing to be bound by any particular theory, in certain embodiments, the connections between the trigeminal nerve and the locus coeruleus, thalamus, amygdala, anterior cingulate, and other central nervous system structures as described above may be relevant to a potential role of the trigeminal nerve in neuropsychiatric disorders, including mood (such as depression), anxiety (such as post-traumatic stress disorder) and other cognitive and behavioral disorders. Thus, cutaneous stimulation of the trigeminal nerve could be effective in the treatment of these neuropsychiatric disorders.

For a discussion of certain embodiments of methods, systems and devices using cutaneous electrodes according to aspects of the present disclosure, reference is now made to FIGS. 2A-5, which show various embodiments of the systems and devices that may be used for the cutaneous stimulation of the superficial branches of the trigeminal nerve and methods of using the same.

According to one aspect of the present disclosure, a method of treating neuropsychiatric disorders using trigeminal nerve stimulation ("TNS") is provided. Broadly speaking, the method of treating neuropsychiatric disorders by TNS comprises positioning external electrodes over or near at least one of the foramina or branches of the trigeminal nerve (FIGS. 1A and 1B), and stimulating the electrodes using a stimulator for a fixed time at specified operational parameters. The electrodes need not be applied at the main branch of the nerve, they can be applied in the area of the skin supplied by that nerve, which may be inches away from the main branch of the nerve. In one embodiment, the external electrodes are positioned over the foramina of the supraorbital or ophthalmic nerves (FIG. 1A, Foramen 1) since unilateral stimulation or bilateral stimulation of the trigeminal nerve is achievable by placing single or separate electrodes on the right and/or left sides (e.g. by placing an electrode assembly, such as two separate electrodes, a single paired electrode or two pairs of electrodes, each electrode having at least one contact, over the forehead or other region of the patient's face). In one embodiment, the electrode assembly is configured for unilateral stimulation. In one embodiment, the electrode assembly is configured for bilateral stimulation. In some embodiments, bilateral stimulation may offer similar or better efficacy than unilateral stimulation because the function of different brain structures may not be the same on right and left (e.g. verbal expression is most commonly localized to speech centers in the left hemisphere, and injury there produces catastrophic loss of the ability to speak, while damage to the corresponding region on the right does not produce this profound loss of function, but may alter subtle functions). There may also be synergistic effects that arise with bilateral stimulation. In some embodiments, two separate electrodes or a single paired electrode may be placed over the forehead. In alternative embodiments, the electrode can be positioned over the foramina of the infraorbital foramen (infraorbital or maxillary nerves) (FIG. 1A, Foramen 2) or the mentalis foramen (mentalis or mandibular nerves) (FIG. 1B, Foramen 3). In yet other embodiments, the stimulation can be unilaterally applied to one foramen of the trigeminal nerves. In other embodiments, the method of treating neuropsychiatric disorders comprises positioning external electrodes over a plurality of foramina and simultaneously stimulating different trigeminal nerves. In other embodiments, electrodes may be positioned at a region of the patient's face (on the right and/or left side) corresponding with the supratrochlear nerve, infratrochlear nerve, zygomaticotemporal, zygomaticofacial, zygomaticoorbital, nasal, and/or auriculotemporal nerves and/or their respective foramina.

According to one aspect of the present disclosure, the method of treating psychiatric disorders by TNS comprises selecting patient specific values for the operational parameters for the stimulation of each individual patient within a defined range. In one embodiment, the values of the operational parameters are selected such that a patient will experience a stimulation sensation, such as a mild tingling over the forehead and scalp without being in discomfort or in pain. In one embodiment, the values of the operational parameters are selected such that skin irritation, burns, and undesired effects on the brain, and/or the cranial nerves are minimized. In one embodiment, the method of selecting operational parameters comprises evaluating variables such as the configuration and size of the electrode, the pulse duration, the electrode current, the duty cycle and the stimulation frequency; which are important factors in ensuring that the total charge, the charge density, and charge per phase are well within accepted limits for the skin, nerve and brain. For example, to minimize skin irritation, it is not sufficient to merely state the total current, but the current density needs to be defined. Additionally, selection of the electrical stimulation parameters, electrode design, and inter-electrode distance are chosen such that the electrical stimulation zone includes the ophthalmic or other cranial nerves (approximately 3-4 mm below the skin surface), while preventing or minimizing current penetration beneath the skull bone as described above.

As described in more detail below with respect to FIGS. 2A-5, the electrodes connect to leads for conveying the electrical stimuli from a neurostimulator. In some embodiments, the neurostimulation may be provided using an electrical neurostimulator at the following exemplary settings: frequency 20-150 Hz, current 1-10 mA, pulse duration (pulse width) of 50-250 microseconds, a duty cycle of 10% to 50%, for at least one hour per day. For patient comfort and low power consumption, stimulation parameters at the lower end of these ranges may be used. In other embodiments, different values of the operational parameters may be used. In alternative embodiments, a single external electrode can be used. In some embodiments, as described in more detail below, a portable external stimulator, which can be attached to a patient's clothing, is used.

Figure 2:
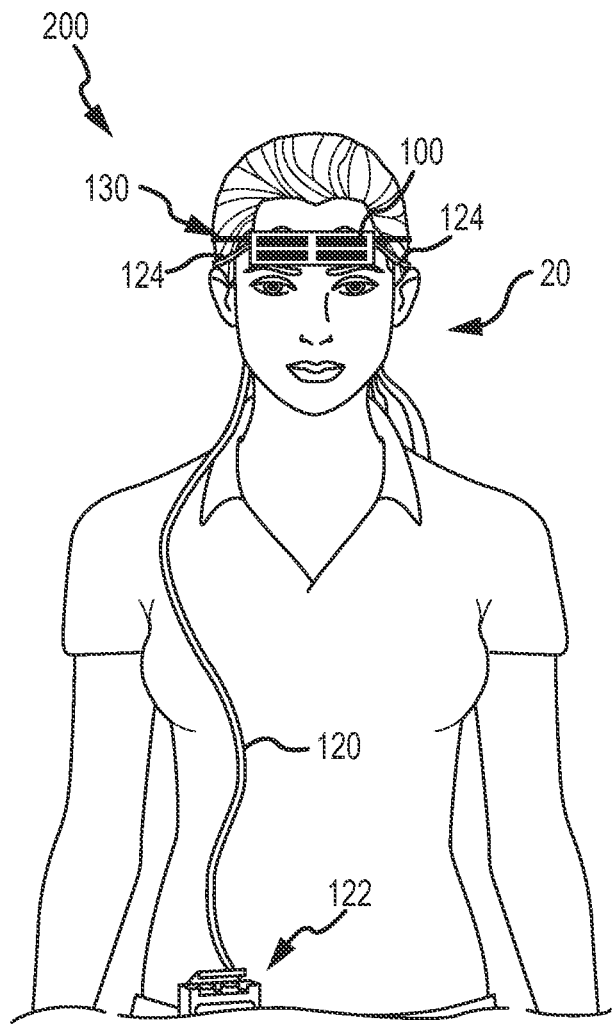
FIG. 2 shows an embodiment of a system including an electrode assembly provided according to aspects of the present disclosure.

In one embodiment, as can be understood from FIGS. 2-5, a system 200 for treatment of neuropsychiatric disorders via TNS includes an electrode assembly 100, electrical cable or wire 120 and an external neurostimulator or pulse generator 122. In some embodiments, the pulse generator may be an internal pulse generator. The electrode assembly may be configured for the bilateral simultaneous and asynchronous stimulation of the ophthalmic nerves. The neurostimulator or pulse generator may be any type of appropriate stimulating, signal-generating device. In the illustrated embodiment, the generator 122 is portable and attached to the belt of a patient 20. However, either a portable or non-portable pulse generator may be used. As shown in FIG. 2, the electrode assembly 100 is connectable to an external stimulator 122 either by lead wires 124 connected to an electrical cable 120 or wirelessly. That is, in one embodiment, the electrical cable or wire 120 is configured to provide a physical and electrical link between the generator 122 and the electrode assembly 100 via lead wires 124. In other embodiments, the generator 122 and the electrode assembly 100 communicate wirelessly (i.e. the wire 120 and leads 124 are not used). The system 200 or elements thereof, such as the electrode assembly 100, may be part of a kit. In some embodiments, the kit may also include instructions for placement of the electrode system and/or system. In some embodiments, the kit may also include instructions for treatment of a neuropsychiatric disorder according to a method as disclosed herein.

In some embodiments, the system 200 may also include a regulation device to ensure safe use of the system. The regulation device is configured to be attached to the pulse generator 122 and is configured to govern the maximum charge balanced output current below approximately 30-50 mA to minimize current penetration to the brain and increase patient tolerance. The regulation device may be internally programmed to range from 0.255.0 mA, 0-10 mA, 0-15 mA, depending on the surface area, placement, and orientation of the electrode, and whether the electrode is stimulating near or adjacent to the skull, or away from the skull, (mentalis), where current ranges may be higher or lower. Current TENS units stimulate with maximum output currents of up to 100 mA's, which result in currents which may penetrate the skull and which may not be well tolerated.

In some embodiments, the electrode assembly 100 further includes a retainer element 130 configured to secure the electrode assembly to a patient's forehead. In one embodiment, the retainer element 130 can be an elastic band or strap. In alternative embodiments, the electrode assembly 100 can be secured in place by a hat or a cap which also serves to conceal the electrode assembly from view. In still other embodiments, the electrode assembly may be secured by adhesive, such as an adhesive strip, an adhesive backing surrounding the conducting area or an adhesive conductive gel.

In some embodiments, the electrode assembly comprises an electrode with at least one contact. In some embodiments, a single electrode may have a plurality of contacts. In some embodiments, the electrode assembly comprises pair of electrodes with a pair of contacts. In some embodiments, the electrode assembly may be a strip electrode with at least one contact. In some embodiments, the strip electrode may include a plurality of contacts.

Figure 3A:
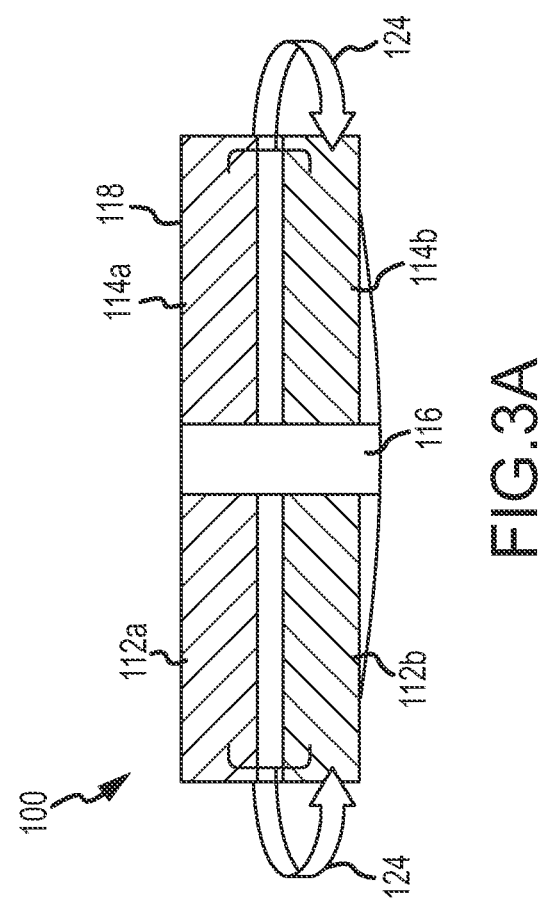
FIG. 3A depicts an enlarged view of the electrode assembly of FIG. 2.
Figure 3B:
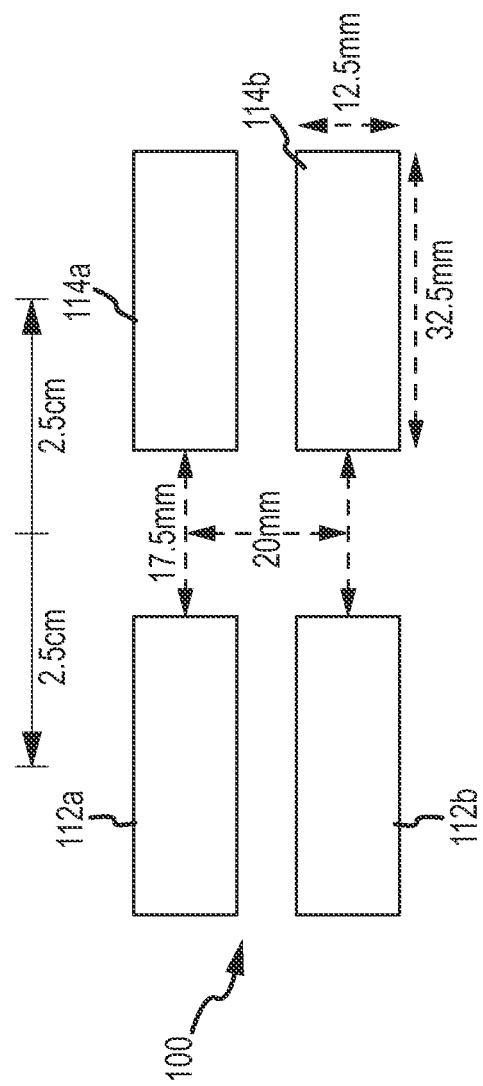
FIG. 3B depicts representative dimensions of the electrode assembly of FIG. 3A.

The electrode assembly 100 shown in FIGS. 2-3B is also referred to as a bilateral supraorbital electrode. As illustrated in FIGS. 2-3B, the electrode assembly 100 includes a first pair of contacts 112a, 112b for placement on a first region of the patient's face, and a second pair of contacts 114a, 114b for placement on a second region of the patient's face. In some embodiments, the first region is the right side of the patient's face and the second region is the left side of the patient's face. The first pair of contacts comprises a first upper contact 112a and a first lower contact 112b, while the second pair of contacts comprises a second upper contact 114a and a second lower contact 114b. The first and second contact pairs are connected to each other by an insulative connection region 116. The electrode assembly 100 comprises an inner contact surface 118 that comes into contact with a patient's skin at four contact areas, each corresponding to one of the four contacts 112a, 112b, 114a, 114b. The inner contact surface 118 comprising the four contact areas includes a buffered gel-like adhesive that provides good electrical conductivity with minimum skin irritation, an example of such gel includes the commercially available hydrogels from AmGel Technologies (AmGel Technologies, Fallbrook, Calif., USA).

In one embodiment, the electrode assembly 100 is configured to stimulate both the right and left ophthalmic nerves either simultaneously or asynchronously. The insulative connection region 116 serves to assist a patient in lining up the electrode assembly 100 with the midline of the nose to ensure proper placement of the electrode assembly 100 over both ophthalmic nerves, which lie on the average about 2.1 to 2.6 cm from the nasal midline of an adult patient. Thus, the electrode assembly can be placed accurately (e.g. by the patient) without knowledge of the location of the ophthalmic nerve or key landmarks relative to the nerve, thereby reducing the possibility of inadequate stimulation due to errors in positioning of the electrodes.

Figure 4A:
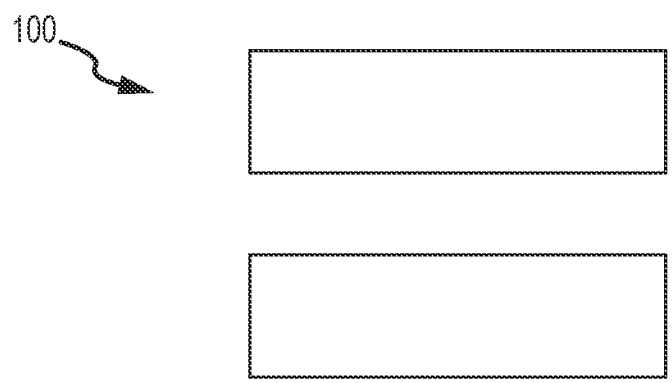
FIGS. 4A-4C depict various embodiments of the cutaneous electrode assembly of FIG. 2.
Figure 4B:
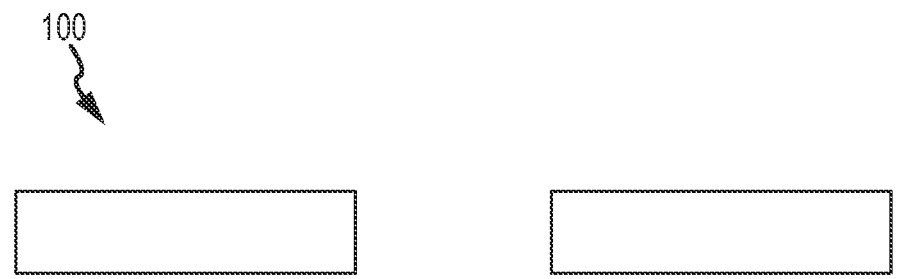
Figure 4C:
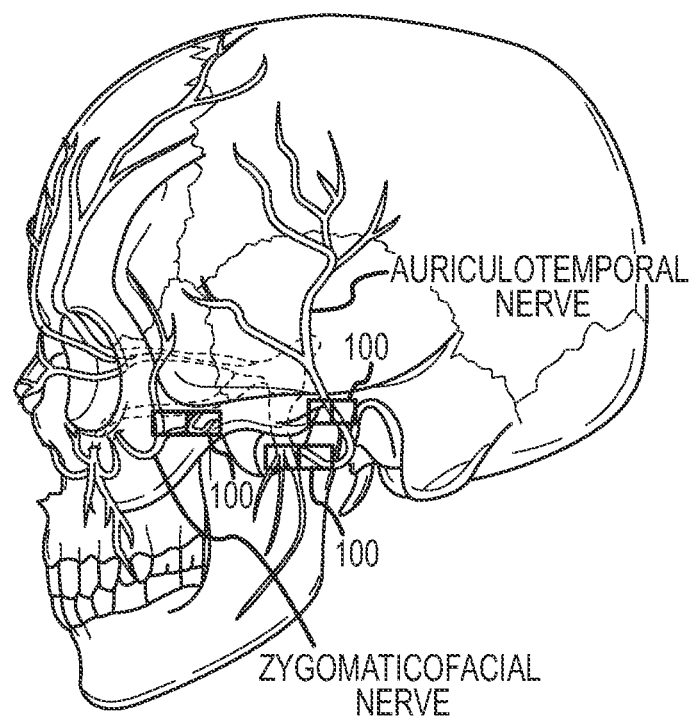

The placement of the first contact pair 112a, 112b and the second contact pair 114a, 114b on opposite sides of the nasal midline assures that stimulation current moves orthodromically or in the direction of the afferent ophthalmic or supraorbital nerve. Furthermore, this configuration of the 112a/112b and 114a/114b to be stimulated independently and/or unilaterally, as the response to stimulus may be localized and thus varied from one side of the midline to the other side. That is, the presently disclosed electrode assembly permits individual adjustment of current for the first and second regions or right and left sides, as applicable, thereby reducing asymmetric stimulation and/or perceived asymmetric stimulation. FIGS. 4A-4C illustrate other embodiments of the electrode assembly 100, which configurations may be used to stimulate the right and/or left ophthalmic nerve and/or other branches of the trigeminal nerve as disclosed herein, such as the zygomaticofacial and/or the auriculotemporal nerves. It can be appreciated that a single electrode with one or more contacts or multiple electrodes with one or more contacts may be used. The bilateral supraorbital electrode is specially configured for bilateral supraorbital stimulation. It is scalable based on the location of use, stimulation parameters and input from computer modeling so as to negate or minimize or render safe, current penetration into the brain. As skin irritation may occur, a similar configuration could be applied unilaterally, so as to provide relief to one side of the forehead, to promote skin tolerability and to reduce the risk of irritation. Other configurations of size and inter electrode distance can be conceived for different branches of the trigeminal nerve, as shown in FIGS. 4A-4C. In one embodiment, a strip electrode with at least two contacts may be used to stimulate the auriculotemporal and/or zygomaticofacial nerve. In other embodiments, two separate electrodes may be used to stimulate the auriculotemporal and/or zygomaticofacial nerve.

For stimulations wherein electrical pulses of a single polarity (monophase—either all positive pulses or all negative pulses) are generated, the upper contacts 112a, 114a and lower contacts 112b, 114 have fixed polarities. For stimulations wherein electrical pulses of alternating polarities (biphase—alternating positive and negative pulses or pulse trains) are generated, the upper contacts 112a, 114a and lower contacts 112b, 114b have alternating polarities. Also, the inferior electrode typically serves as the cathode for the leading phase of the stimulating pulse. In the case of a monophasic stimulation, the inferior electrode generally becomes the cathode.

As can be understood from FIG. 3B, each of the contacts 112a, 112b, 114a, 114b is sized to deliver an electrical pulse over a large enough surface area to minimize any skin injury due to excess current density and/or charge density, and to minimize or eliminate current penetration beyond the inner surface of the skull bone. The distance between the first contact pair 112a, 112b and the second contact pair 114a, 114b is configured to stimulate the ophthalmic nerves while minimizing or eliminating current delivery to the surface of the brain. In one embodiment, the mid-point of each of the contacts is approximately 2.5 cm (range 1.5 cm to 3.5 cm) from the nasal midline. The electrode size and the inter-electrode distance may vary for children and adults, males and females based on anatomical differences. In one embodiment, the electrode is approximately 32.5 mm in length by 12.5 mm in height and the inter-electrode distance between, for example, the upper pair of electrodes 112a, 114a is 17.5 mm and the inter-electrode distance between, for example, the upper electrode 112a and the lower electrode 112b is 20 mm In other embodiments, the length of the electrode may be greater than or less than 32.5 mm and greater than or less than 12.5 mm in height. In still other embodiments, the inter electrode distance can be in a range greater than 20 mm and/or less than 17.5 mm. In various embodiments, the surface area of each of the contacts 112a, 112b, 114a, and 114b can be within a range of about 0.5 cm² to about 20 cm². In various embodiments, the distance between the contacts 112a and 112b and the distance between contacts 114a, and 114b can be in a range of about 0.5 cm to about 10 cm. Those of skill in the art will recognize that one or more of the above distances can be used as a border of a range of distances.

Figure 5:
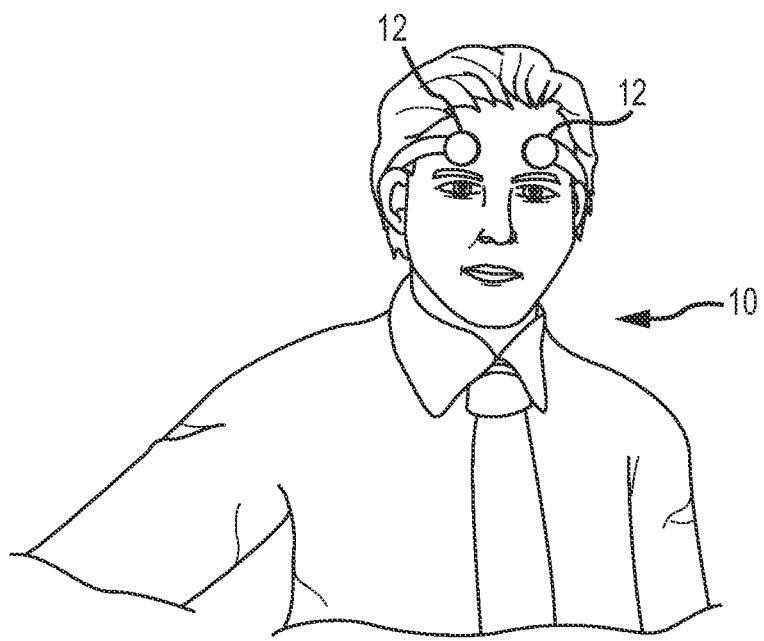
FIG. 5 shows another embodiment of an electrode assembly that may be used with the system of FIG. 2.

FIG. 5 illustrates another embodiment of the electrode assembly 100. As shown in FIG. 5, a patient 10 is wearing two separate electrodes 12 on the forehead, one over each eyebrow, corresponding to the foramina of the ophthalmic nerves.

Those skilled in the art will appreciate that various adaptations and modifications of the above-described embodiments of the electrode assembly 100 are within the scope and spirit of the present disclosure. For example, one embodiment of the present device comprises a unilateral electrode assembly configured for the unilateral stimulation of ophthalmic nerves. Also, the instant electrode assembly can also be configured for the stimulation of the maxillary nerves or the mandibular nerves. Alternatively, an electrode assembly configured for the simultaneous stimulation of a plurality of trigeminal nerve branches is also within the scope of the present disclosure. In one embodiment, the system or electrode assembly as disclosed herein may be configured to stimulate the auriculotemporal nerve. In one embodiment, the system or electrode assembly as disclosed herein may be configured to stimulate the zygomaticofacial nerve.

In use, the electrode assembly 100 is positioned over the forehead of the patient 20 such that the insulative connection region 116 lines up with the midline of the patient's nose. In some embodiments, the electrode assembly 100 is placed over the supraorbital foramina, located over the orbital ridge approximately 2.1-2.6 cm lateral to nasal midline. The electrode assembly 100 may then be connected to the external neurostimulator 122 via lead wires 124 and the electrical cable 120. In other embodiments, the electrode assembly 100 is connected to the neurostimulator 122 via a wireless connection. Stimulation according to patient specific operational parameters as determined according to the methods described herein is then applied.

According to one aspect of the present disclosure, there is provided a method of treatment of neuropsychiatric disorders using the electrode assembly 100, as described above. In one embodiment, the method of treating psychiatric disorders comprises positioning the electrode assembly 100 to the forehead of a patient, connecting the electrode assembly 100 to an external stimulator 122, and stimulating the electrode assembly 100 at defined values of the operational parameters as disclosed herein.

According to one aspect of the present disclosure, there is provided a method of treatment of neuropsychiatric disorders using an embodiment of the electrode assembly as described herein. In one embodiment, the method of treating psychiatric disorders comprises positioning the electrode assembly at a first region of a face of a patient, connecting the electrode assembly to an external stimulator, and stimulating the electrode assembly at defined values of the operational parameters as disclosed herein. In one embodiment, the first region is a region corresponding to the auriculotemporal nerve. In one embodiment, the first region is a region corresponding to the zygomaticofacial nerve. In one embodiment, the first region is a region corresponding to the supraorbital nerve.

In one embodiment, the bilateral supraorbital electrode 100 illustrated in FIGS. 2-3A is stimulated at a stimulus frequency between about 20 Hz and about 300 Hz, at a pulse duration between 50 microseconds (μsec) and 250 μsec, at an output current density of less than 25 mA/cm² and an output charge density of less than 10μ Coulomb/cm² at the cerebral cortex for at least one-half to one hour per day. In general, the stimulation would yield no or negligible charge densities at the cerebral. In some cases, stimulation can be provided for less than one-half hour per day. Those of skill in the art will recognize that one or more of the above parameters can be used as a border of a range of parameters.

In various embodiments, the stimulation is delivered at a specific pulse width or range of pulse widths (or pulse duration). The stimulation can be set to deliver pulse widths in any range within a lower limit of about 10 microseconds and an upper limit of about 3 seconds. In various embodiments, the stimulation can be set to deliver pulse widths in the range greater than and/or less than one or more of 50 μs, 60 μs, 70 μs, 80 μs, 90 μs, 100 μs, 125 μ, 150 μs, 175 μs, 200 μs, 225 μs, 250 μs, up to 500 μs. Those of skill in the art will recognized that one or more of the above times can be used as a border of a range of pulse widths.

In some embodiments, the stimulation amplitude is delivered as a voltage or current controlled stimulation. In other embodiments it can be delivered as a capacitive discharge. In various embodiments, the current amplitude can be in any range within a lower limit of about 300 μA and an upper limit of about 30 mA-35 mA, depending on the surface area of the electrodes, inter-electrode distance, the branch(es) stimulated, and the modeling data as described above. In various embodiments, the amplitude can be in a range greater than and/or less than one or more of 50 μA, 75 μA, 100 μA, 125 μA, 150 μA, 175 μA, 200 μA, 225 μA, 250 μA, 275 μA, 300 μA, 325 μA, 350 μA, 375 μA, 400 μA, 425 μA, 450 μA, 475 μA, 500 μA, 525 μA, 550 μA, 575 μA, 600 μA, 625 μA, 650 μA, 675 μA, 700 μA, 725 μA, 850 μA, 875 μA, 900 μA, 925 μA, 950 μA, 975 μA, 1 mA, 2 mA, 3 mA, 4 mA, 5 mA, 6 mA, 7 mA, 8 mA, 9 mA, 10 mA, 11 mA, 12 mA, 13 mA, 14 mA, 15 mA, 16 mA, 17 mA, 18 mA, 19 mA and 20 mA. Those of skill in the art will recognize that one or more of the above amplitudes can be used as a border of a range of amplitudes.

In various embodiments, the stimulation can be delivered at one or more frequencies, or within a range of frequencies. The stimulation can be set to be delivered at frequencies in any range within an upper limit of about 500 Hz and a lower limit of about 10 Hz. In various embodiments, the stimulation can be set to be delivered at frequencies less than, and/or greater than one or more of 50 Hz, 45 Hz, 40 Hz, 35 Hz, 30 Hz, 25 Hz, 20 Hz, 15 Hz, or 10 Hz. In various embodiments, the stimulation can be set to be delivered at frequencies greater than, and/or less than, one or more of 20 Hz, 30 Hz, 40 Hz, 50 Hz, 60 Hz, 70 Hz, 80 Hz, 90 Hz, 100 Hz, 125 Hz, 150 Hz, up to 300 Hz. Those of skill in the art will recognize that one or more of the above frequencies can be used as a border of a range of frequencies.

In various embodiments, the stimulation is delivered at a specific duty cycle or range of duty cycles within a range from 100% down to about 5%. In various embodiments, the stimulation can be set to be delivered at a duty cycle in the range greater than and/or less than one or more of 5%, 10%, 15%, 20%, 25%, 30%, 35%, 40%, 45%, 50%, 55%, 60%, 65%, 70%, 75%, 80%, 85%, 90%, 95%, or 100%. In some embodiments, to ensure preservation of the nerve, a duty cycle of 10% to 50% may be preferable. In some embodiments, duty cycles up to 100% may be useful in particular circumstances. Those of skill in the art will recognize that one or more of the above percentages can be used as a border of a range of duty cycles.

In other embodiments, different values of the operational parameters may be used. In one embodiment, the values of the operational parameters are selected such that a patient will experience a stimulation sensation, such as a mild tingling over the forehead and scalp without being in discomfort or in pain. The neurostimulation parameters are important factors in the treatment method. In one embodiment, the values of the operational parameters are selected to minimize skin irritation, burns, undesired effects on the brain and/or the ophthalmic nerves. In one embodiment, the method of selecting operational parameters comprises evaluating variables such as the configuration and size of the electrode, the pulse duration, the electrode current, the duty cycle and the stimulation frequency, each of which are important factors in ensuring that the total charge, the charge density, and charge per phase are well within accepted safety limits for the skin, nerve and brain. For example, to minimize skin irritation, it is not sufficient to merely consider the total current, but the current density needs to be defined. Additionally, it is important to select the electrical stimulation parameters, electrode design, and inter-electrode distance, such that the electrical stimulation zone includes the ophthalmic nerve (approximately 3-4 mm deep), or other target nerve, while preventing or minimizing current penetration beneath the skull bone.

The stimulation is carried out at the above-described values of the operational parameters. The values of the operational parameters are advantageously selected such that a patient will experience a stimulation sensation, such as mild tingling over the forehead and scalp, without causing the patient unbearable discomfort or pain. These values may vary according to the treatment of interest; however, the systems and devices disclosed herein stimulate at parameters where current penetration below the surface of the skull and/or into the brain is prevented or minimized In some embodiments, an external device may be used to identify the location of the branch or branches of the trigeminal nerve that will be targeted in an individual patient for stimulation by the implanted electrode assembly disclosed herein. The external device may be used for mapping and targeting the desired branch or branches of the trigeminal nerve and for identifying the individual stimulation parameters that are optimal for efficacy and safety. In one embodiment, the device may include a plurality of external (transcutaneous) TNS electrodes. The practitioner approximates the location of the target branch and affixes the electrodes to the patient's skin above the target location. Stimulation may be applied and the actual location or preferred (optimal) stimulation location of the target branch or branches may be determined Stimulation parameters may also be established. Once the location and/or stimulation parameters have been established via the external device, that data may be used to help guide the placement of the implanted electrodes for an individual patient and to establish the customized stimulation parameters for that patient.

In addition, the use of external electrodes for stimulation of the trigeminal nerve may identify individuals who are likely to derive therapeutic benefit from a minimally invasive system in addition to the optimal specific locations and parameters of stimulation based on person-to-person variability. Various neurodiagnostic, imaging, or cutaneous nerve mapping methods may be able to delineate differences in individual anatomy to optimize stimulation for efficacy and/or safety. Furthermore, the use of a minimally invasive system may allow screening and identification of those individuals who are likely to derive benefit from other implantable systems, such as deep brain stimulation. This can be conceptualized as linking the three approaches as stage I (external TNS of the trigeminal nerve), stage II (implanted TNS of the superficial trigeminal nerve), and stage III (deep brain stimulation), such that stage I can screen for stage II, and stage II for stage III. By monitoring a patient for evidence of useful therapeutic effect, such as by reduction in the severity of symptoms, the results of treatment at one stage may be used to judge the likely effect of treatment with a more invasive treatment from a higher stage.

A method of evaluating the use of trigeminal nerve stimulation for treatment of a neuropsychiatric disorder in a patient is disclosed herein. The method may include applying a cutaneous system for stimulation of the trigeminal nerve to the patient and monitoring the patient for at least one of evidence of a useful therapeutic response or evidence of tolerability of TNS treatment, providing a subcutaneous electrode assembly or system, and implanting the subcutaneous electrode assembly or system in the patient for treatment of a neuropsychiatric disorder.

A method of evaluating the use of deep brain stimulation for treatment of a neuropsychiatric disorder in a patient is disclosed herein. The method may include applying a cutaneous system for stimulation of the trigeminal nerve to the patient and monitoring the patient for at least one of evidence of a useful therapeutic response or evidence of tolerability of TNS treatment thereby generating external measurement criteria, providing a subcutaneous electrode assembly or system, implanting the subcutaneous electrode assembly or system in the patient for treatment of a neuropsychiatric disorder, monitoring the patient for at least one of a useful therapeutic response or tolerability of the implanted device, thereby generating extracranial measurement criteria, and analyzing the external measurement criteria and extracranial measurement criteria to determine whether the patient will benefit from deep brain stimulation.

The following examples are presented to set forth more clearly the subject matter of this disclosure without imposing any limits on the scope thereof and to illustrate the clinical benefits of trigeminal nerve stimulation for the treatment of neuropsychiatric disorders. In the first example, patients with major depressive disorder were treated by TNS with external cutaneous electrodes. In the second example, a patient was treated using cutaneous electrodes for bilateral supraorbital stimulation.

EXAMPLE 1

Figures 6A, 6B:
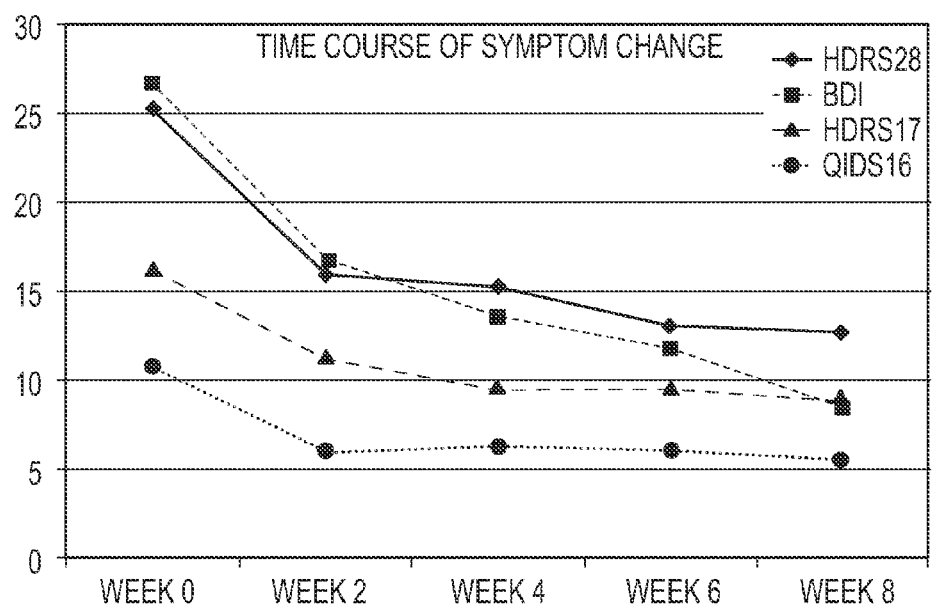
FIG. 6A is a table showing an average of the results of four assessment tests pre-treatment and post treatment of a treatment study for psychiatric disorders using aspects of the present disclosure.
FIG. 6B is a bar graph of the data shown in FIG. 6A.
Figure 6C:
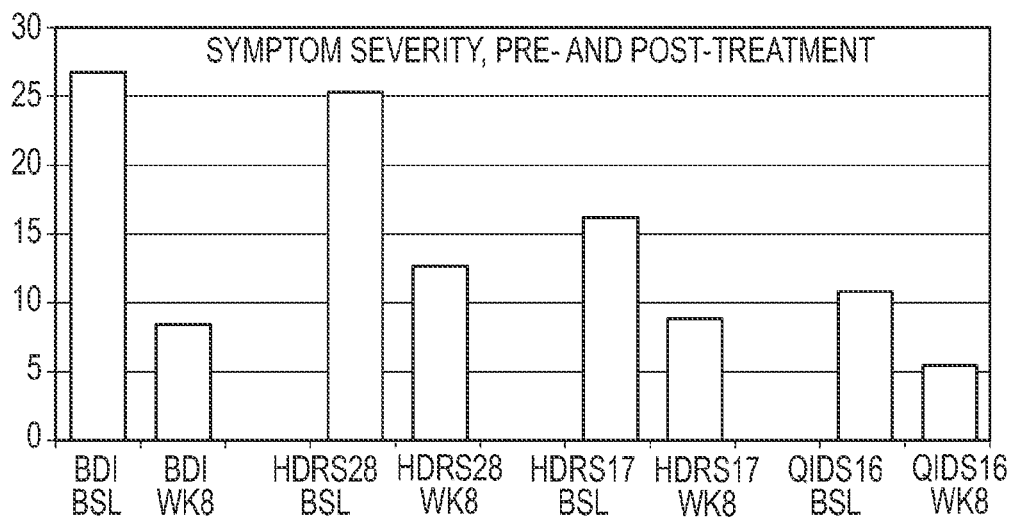
FIG. 6C is a graph illustrating the change over time of the data shown in FIG. 6A.

FIGS. 6A-6C illustrate the results from a pilot study of external trigeminal nerve stimulation for the treatment of depression. Subjects with major depression who met inclusion and exclusion criteria were followed for 8-weeks in an open label (unblinded) study conducted at UCLA.

Inclusion Criteria were: Age 18-65 years old who met DSM-IV criteria for an acute, recurrent episode of Major Depressive Disorder (MDD) and were in a major depressive episode (MDE) of moderate severity. Other inclusion criteria were: the current MDE must be ≥4 months in duration, no response to at least one antidepressant over at least six weeks during the current MDE, and concomitant use of at least one antidepressant. All had prominent residual symptoms, with mean Hamilton Depression Rating Scale (HDRS-28) scores at study entry of 25.4 (3.9 s.d.), range 19 to 29. Subjects placed stimulating electrodes over the supraorbital branches of the trigeminal nerve for at least 8 hours per day (primarily while asleep), with current adjusted to maintain comfortable levels. Five subjects completed the trial. Primary outcome was change in HDRS at 8 weeks.

Exclusion criteria were: current pregnancy; meeting DSM-IV criteria for atypical or psychotic or bipolar depression; a history of schizophrenia, schizoaffective disorder, or other non-mood disorder psychosis; a current secondary DSM-IV diagnosis (or signs) of delirium, dementia, amnestic disorder or other cognitive disorder; clinically significant current suicidal intent; significant cardiac, medical or progressive neurological or medical illness; facial pain or trigeminal neuralgia; a VNS or other implantable electrical device such as a pacemaker; current use of a TENS or VNS unit, or history of non-compliance.

All subjects received unblinded TNS augmentation (adjunctive) treatment for at least 8-hours each day. Assessments were made at study intake, and at weeks 2, 4, 6, and 8 in the acute treatment phase. Subjects who wished to continue the treatment were allowed to participate in an optional 6-month long-term extension phase with monthly monitoring visits.

Subjects underwent stimulation using an electrical stimulator, such as for example the EMS Model 7500 commercially available from TENS Products, Inc. (www.tensproducts.com) operated at a frequency of 120 Hertz, a current less than 20 mA, a pulse duration of 250 µsec, and a duty cycle at 30 seconds on and 30 seconds off, for a minimum of 8 hours per day.

Prior to initiating treatment and at subsequent follow-up assessment visits, the symptom severity of each subject was quantified using the Hamilton Depression Rating Scale (HDRS, scored using both 17- and 28-item versions), the Beck Depression Inventory (BDI), and the Quick Inventory of Depressive Symptomatology (QIDS), with the group average values on each of these scales being tabulated in the table shown in FIG. 6A. All three are assessment instruments designed to measure the severity of depression. The HDRS is a well-established rating scale instrument which is filled out by a clinician after interviewing and observing the individual subject in order to measure the severity of depression; in this study, ratings on all 28 items (questions) were made, and the scale was scored according to standard methods using all items ($HDRS_{28}$) and the standard subset of 17 items ($HDRS_{17}$). The BDI is a 21-question multiple choice self-report survey that is used to measure the severity of depression. The $QIDS-C_{16}$ is a 16-question clinician-rated survey that is used to measure the severity of depression. Each of these scales affords different strengths and limitations in assessing a patient's symptom severity (e.g. BDI emphasizes cognitive symptoms of depression, while the HDRS weights neurovegetative symptoms prominently), and all are commonly used in clinical trials in major depression; the use of multiple scales allowed a more comprehensive assessment of the effects of trigeminal nerve stimulation than any single scale in this initial study of this treatment for major depression.

As shown in FIG. 6A, and graphically illustrated in FIGS. 6B and 6C, decreases in $HDRS_{28}$ were significant, from 25.4 (3.9 s.d.) at entry to 13.6 (6.3 s.d.) at week 8 (2-tail t-test p<0.01, Cohen's d 2.4). Responses on the BDI similarly declined, from 26.8 (8.1) to 10.6 (4.9) (p<0.01, d 2.3). Decreases on the 16-item clinician-rated QIDS were also significant, decreasing from 10.8 (3.4) to 5.5 (4.4) (p<0.05, d 1.3). Thus, significant decreases in symptom severity were achieved in the 8 weeks of acute TNS treatment. Furthermore, changes in symptoms occurred across all symptom areas, such as depressed mood, anxiety, sleep, and energy. These findings support the use of TNS treatment which may also have use as an adjunct to pharmacotherapy when medications have failed to produce remission of symptoms.

EXAMPLE 2

FIG. 7 summarizes current, charge, current density and charge density recorded in a subject during exposure to cutaneous stimulation of the supraorbital nerve. FIG. 7 illustrates representative parameters for bilateral supraorbital stimulation recorded in a subject using an EMS 7500 stimulator, 120 HZ, 150-250 µsec, Tyco superior silver electrodes 1.25", placed one inch from the midline above the eyebrows. Data recorded with Fluke Oscilloscope, 50 mV/div, resistor=10.1Ω. In general, these findings show that, as the pulse width increased, the maximum tolerable current decreased.

Cutaneous electrical stimulation of the supraorbital branch of the trigeminal nerve with round 1.25-inch TENS patch electrodes results in current densities and charge density/phase that are well within the limits of safety. In general, the maximum current comfortably tolerated by TNS patients studied previously is approximately 25 mA, and patients typically are stimulated at an amplitude setting well below 25 mA (6-10 mA).

The 1.25-inch TENS electrodes are circular electrodes with a radius of 1.59 cm. The surface area can be calculated as $A=\pi r^2=[\pi]*[1.59 \text{ cm}]^2=7.92 \text{ cm}^2$. Using these electrodes, typical stimulation current ranges from 6-10 mA at pulse durations of 150-250 µsec.

Current Density: In a typical subject, stimulation currents of 6-10 mA result in current densities ranging from 0.76 to 1.3 $mA/cm^2$. McCreery et al have established a maximum safe current density of 25 mA/cm at the stimulating electrode for transcranial electrical stimulation. Assuming even higher currents of up to 25 mA with electrodes of surface area 7.92 $cm^2$, current densities may range to a maximum of 3.16 $mA/cm^2$. From 0.76 $mA/cm^2$ to 3.16 $mA/cm^2$, TNS delivers a current density 8-33 times less than the maximum safe allowable current density. Charge Density (Charge density/phase): Yuen et al have identified a safe limit for charge density/phase delivered at the cerebral cortex of 40 $\mu C/cm^2$. [Yuen et al 1981] and more recently McCreery et al. (McCreery et al 1990) have identified 10 $\mu C/cm^2$ as the safe limit. Assuming 10 mA at 250 µsec, the charge density/phase is $[0.010 \text{ A}] \times [250 \text{ µsec}]/7.92=0.32 \mu C/cm^2$ at the stimulating electrode. Assuming even higher levels of stimulation, 25 mA at 250 µsec, the maximum charge density per phase is 0.79 $\mu C/cm^2$. At these levels, the charge density is generally 12 to 120 fold less at the stimulating electrode than the maximum allowed at the cerebral cortex. Since the cortex is a minimum of 10-13 mm from the stimulating electrodes, and given the interposed layers of skin, fat, bone, dura, and CSF, the actual charge densities will be significantly lower. This is of importance in avoiding the undesired passage of current directly through brain tissue as a bulk conductor.

As shown in FIG. 7, stimulation intensity responses in a subject with electrodes of surface area 7.92 cm2, at pulse durations between 150-250 μsec, results in current densities at the scalp well below currently recommended current densities for transcranial stimulation, which are 25 mA/cm$^2$, and charge densities at the scalp significantly lower than safe charge densities at the cerebral cortex (0.15-0.18 μC/cm$^2$).

From the foregoing discussion, it will be appreciated that the invention can be embodied in various ways which include, but which are not limited to, the following:

1. A cutaneous electrode assembly for trigeminal nerve stimulation for treatment of a neuropsychiatric disorder, the cutaneous electrode assembly comprising: a first pair of contacts configured for placement on a first region of a patient's face; a second pair of contacts configured for placement on a second region of a patient's face; and an insulating connection region connecting the first pair of contacts and the second pair of contacts, wherein the first pair of contacts and the second pair of contacts are configured to contact a portion of the patient's face overlying the cutaneous distribution of at least one branch of the trigeminal nerve and to stimulate said branch of said nerve with minimal or no current penetration below the surface of the skull.
2. The cutaneous electrode assembly of claim 1, wherein the at least one branch of the trigeminal nerve is selected from the group consisting of: superficial ophthalmic branch, infraorbital branch, and the mentalis branch.
3. The cutaneous electrode assembly of claim 1, wherein the at least one branch of the trigeminal nerve is a supraorbital nerve.
4. The cutaneous electrode assembly of claim 1, wherein the at least one branch of the trigeminal nerve is an auriculotemporal nerve.
5. The cutaneous electrode assembly of claim 1, wherein the at least one branch of the trigeminal nerve is a zygomaticofacial nerve.
6. The cutaneous electrode assembly of claim 1, further comprising a retainer element configured to secure the electrode assembly to a patient's forehead.
7. The electrode assembly of claim 1, wherein the neuropsychiatric disorder is depression.
8. A system for trigeminal nerve stimulation for treatment of a neuropsychiatric disorder or condition, the system comprising: a neurostimulator; and a cutaneous electrode assembly comprising: a first pair of contacts configured for placement on a first region of a patient's face; a second pair of contacts configured for placement on a second region of the patient's face; and an insulating connection region connecting the first pair of contacts and the second pair of contacts, wherein the first pair of contacts and the second pair of contacts are configured to contact a portion of the patient's face overlying the cutaneous distribution of at least one branch of the trigeminal nerve.
9. The system of claim 8, further comprising a cable and lead wires operably connecting the neurostimulator and the cutaneous electrode assembly.
10. The system of claim 8, further comprising a regulation device configured to regulate current output to minimize or prevent current penetration below the surface of the skull bone.
11. The system of claim 8, wherein the at least one branch of the trigeminal nerve is selected from the group consisting of: superficial ophthalmic branch, infraorbital branch, and mentalis branch.
12. The system of claim 8, further comprising a retainer element configured to secure the electrode assembly to the patient's forehead.
13. The system of claim 8, wherein the at least one branch of the trigeminal nerve is a supraorbital nerve.
14. The system of claim 8, wherein the at least one branch of the trigeminal nerve is an auriculotemporal nerve.
15. The system of claim 8, wherein the at least one branch of the trigeminal nerve is a zygomaticofacial nerve.
16. A kit for trigeminal nerve stimulation for treatment of a neuropsychiatric disorder or condition, the kit comprising: the cutaneous electrode assembly according to claim 1; and instructions for placement of the electrode assembly on a patient for treatment of a neuropsychiatric disorder.
17. The kit of claim 16, further comprising: a neurostimulator; and instructions for applying electrical signals to the electrode assembly for treatment of a neuropsychiatric disorder.
18. A method for treating a neuropsychiatric disorder by trigeminal nerve stimulation, comprising: attaching an electrode assembly to a patient, the electrode assembly comprising: a first pair of contacts configured for placement on a first region of the patient's face; a second pair of contacts configured for placement on a second region of the patient's face; and an insulating connection region connecting the first pair of contacts and the second pair of contacts, wherein the first pair of contacts and the second pair of contacts are configured to contact a portion of the patient's face overlying the cutaneous distribution of at least one branch of the trigeminal nerve; and applying electrical signals to the electrode assembly at specified operational parameters to treat a neuropsychiatric disorder with minimal current penetration below the skull bone.
19. The method of claim 18, wherein the step of applying electrical signals comprises applying electrical signals at a frequency between approximately 20 and 300 Hertz, at a pulse duration between approximately 50 and 500 microseconds, at an output current density of not greater than approximately 25 mA/cm$^2$ and an output charge density of not greater than approximately 10 micro Coulomb/cm$^2$.
20. The method of claim 18 wherein the electrode assembly is attached to the patient so as to contact the skin surface over a supraorbital nerve.
21. The method of claim 18 wherein the electrode assembly is attached to the patient so as to contact the skin surface over an auriculotemporal nerve.
22. The method of claim 18 wherein the electrode assembly is attached to the patient so as to contact the skin surface over a zygomaticofacial nerve.
23. The method of claim 18, wherein the neuropsychiatric disorder is depression.

Those skilled in the art will appreciate that various adaptations and modifications of the above described preferred embodiments may be configured without departing from the scope and spirit of this disclosure. Stimulation of the target nerve may be accomplished by cutaneous application of energy in many forms, such as magnetic or ultrasonic. Therefore, it is to be understood that the subject matter of this disclosure may be practiced other than as specifically described herein.

What is claimed is:

1. A system for trigeminal nerve stimulation for treatment of a neuropsychiatric disorder, the system comprising:

a pulse generator; and a cutaneous electrode assembly in electrical communication with the pulse generator, the assembly comprising:

a first electrode comprising at least one contact configured for cutaneous placement directly over or adjacent an ophthalmic nerve on one side of a patient's forehead, and a second electrode comprising at least one contact configured for cutaneous placement directly over or adjacent a remaining ophthalmic nerve on an opposing side of the patient's forehead.

2. The system of claim 1, further comprising a wire operably connecting the pulse generator and the cutaneous electrode assembly.

3. The system of claim 1, further comprising a regulating device configured to regulate a maximum charge balanced output current through the first and second electrodes below approximately 30-50 mA.

4. The system of claim 1, wherein the neuropsychiatric disorder is selected from the group consisting of: mood disorder, cognitive disorder, behavioral disorder and anxiety disorder.

5. The system of claim 1, wherein the pulse generator is configured to apply electrical signals at a frequency between approximately 20 and 300 Hertz, at a pulse duration between approximately 50 and 500 microseconds, at an output current density of not greater than approximately 25 mA/cm$^2$ and an output charge density of not greater than approximately 10 microCoulomb/cm$^2$ at the cerebral cortex.

6. A system for trigeminal nerve stimulation for treatment of a neuropsychiatric disorder, the system comprising:

a pulse generator; and a cutaneous electrode assembly in electrical communication with the pulse generator, the assembly comprising:

a first electrode contact configured for cutaneous placement directly over or adjacent a trigeminal nerve branch on a patient, and a second electrode contact configured for cutaneous placement directly over or adjacent the trigeminal nerve branch on the patient, wherein the trigeminal nerve branch is selected from the group consisting of the mandibular nerve and the maxillary nerve.

7. The system of claim 6, further comprising a wire operably connecting the pulse generator and the cutaneous electrode assembly.

8. The system of claim 6, further comprising a regulating device configured to regulate a maximum charge balanced output current through the first and second electrode contacts below approximately 30-50 mA.

9. The system of claim 6, wherein the neuropsychiatric disorder is selected from the group consisting of: mood disorder, cognitive disorder, behavioral disorder and anxiety disorder.

10. The system of claim 6, wherein the pulse generator is configured to apply electrical signals at a frequency between approximately 20 and 300 Hertz, at a pulse duration between approximately 50 and 500 microseconds, at an output current density of not greater than approximately 25 mA/cm$^2$ and an output charge density of not greater than approximately 10 microCoulomb/cm$^2$ at the cerebral cortex.

11. A method for treating a neuropsychiatric disorder by trigeminal nerve stimulation, comprising:

applying a first electrode contact for a cutaneous electrode assembly directly over or adjacent to an ophthalmic nerve on one side of the patient's forehead;

applying a second electrode contact for the cutaneous electrode assembly directly over or adjacent to a remaining ophthalmic nerve on an opposing side of the patient's forehead; and driving electrical signals through the first and second electrode contacts at specified operational parameters to treat the neuropsychiatric disorder.

12. The method of claim 11, wherein the step of driving the electrical signals comprises driving the electrical signals at a frequency between approximately 20 and 300 Hertz, at a current of 0.05 to 5 milliamperes (mA) and at a pulse duration of less than or equal to 500 microseconds.

13. The method of claim 11, wherein the step of driving the electrical signals results in an output current density of not greater than approximately 25 mA/cm$^2$ and a charge density of not greater than approximately 10 microCoulomb/cm$^2$ at the cerebral cortex of the patient.

14. The method of claim 11, wherein the neuropsychiatric disorder is selected from the group consisting of: mood disorder, cognitive disorder, behavioral disorder and anxiety disorder.

15. A method for treating a neuropsychiatric disorder by trigeminal nerve stimulation, comprising:

applying a cutaneous electrode assembly directly over or adjacent to a trigeminal nerve branch on a patient; and driving electrical signals through electrode contacts in the cutaneous electrode assembly at specified operational parameters to treat the neuropsychiatric disorder, wherein the trigeminal nerve branch is selected from the group consisting of the mandibular nerve and the maxillary nerve.

16. The method of claim 15, wherein the step of driving the electrical signals comprises driving the electrical signals at a frequency between approximately 20 and 300 Hertz, at a current of 0.05 to 5 milliamperes (mA) and at a pulse duration of less than or equal to 500 microseconds.

17. The method of claim 15, wherein the step of driving the electrical signals results in an output current density of not greater than approximately 25 mA/cm$^2$ and a charge density of not greater than approximately 10 microCoulomb/cm$^2$ at the cerebral cortex of the patient.

18. The method of claim 15, wherein the neuropsychiatric disorder is selected from the group consisting of: mood disorder, cognitive disorder, behavioral disorder and anxiety disorder.

* * * * *